United States Patent [19]

Kaitz

[11] Patent Number: 4,982,750
[45] Date of Patent: Jan. 8, 1991

[54] METHOD OF RECURLING TIGHTLY CURLED HAIR

[75] Inventor: Richard Kaitz, Minneapolis, Minn.

[73] Assignee: Miriam Collins-Palm Beach Laboratories, Co., Minneapolis, Minn.

[21] Appl. No.: 201,564

[22] Filed: Jun. 1, 1988

[51] Int. Cl.$^5$ .............................................. A45D 7/04
[52] U.S. Cl. .................................... 132/204; 132/205; 132/210; 424/72
[58] Field of Search ............... 132/204, 205, 206, 207, 132/210, 211, 202; 424/72

[56] References Cited

U.S. PATENT DOCUMENTS

| | | | |
|---|---|---|---|
| 3,910,289 | 10/1975 | Wajaroff et al. | 132/205 |
| 4,087,518 | 5/1978 | Smith et al. | |
| 4,765,975 | 8/1988 | Iovanni et al. | 132/202 |
| 4,840,791 | 6/1989 | Matthews et al. | 132/202 |
| 4,841,997 | 6/1989 | Petrow | 132/204 |

FOREIGN PATENT DOCUMENTS 2090303  7/1982  United Kingdom ............... 132/204

OTHER PUBLICATIONS

Ahern, West's Textbook of Cosmetology, West Publishing Co., 2nd Ed., (1986) pp. 261, 280–283.

Dalton, The Professional Cosmetologist, West Publishing Co., 3rd Ed., (1985), pp. 315–329.

Balsam et al., Cosmetics: Science and Technology, John Wiley and Sons (publishers), 2nd Ed., vol. 3, p. 123.

Jellinek, Formulation and Function of Cosmetics, John Wiley & Sons (publishers), (1970), pp. 497–505.

*Primary Examiner*—Randall L. Green
*Assistant Examiner*—Paul Prebilic
*Attorney, Agent, or Firm*—Merchant, Gould, Smith, Edell Welter & Schmidt

[57] ABSTRACT

The present invention provides a method by which hair which is tightly curled or kinked can be consistently relaxed and reformed into a looser curl or wave configuration, with substantially less damage to the hair. The process of the present invention includes the steps of: (a) contacting the hair with an aqueous relaxant composition comprising five to ten weight percent monoethanolamine thioglycolate; (b) rinsing the hair; (c) contacting the hair with an aqueous suspending composition; (d) wrapping the hair onto curling rods; (e) contacting the hair with a heat generating composition comprising a first and second solution provided in separate containers; (f) contacting the hair with an oxidizing composition; (g) removing the curling rods; and (h) contacting the hair with an acidic protein final rinse.

18 Claims, No Drawings

METHOD OF RECURLING TIGHTLY CURLED HAIR

FIELD OF THE INVENTION

The present invention relates to the curling or waving of human hair. The present invention relates more particularly to chemically assisted curling or waving of human hair having a flat or oval cross sections.

BACKGROUND OF THE INVENTION

Hair which has a relatively flat or oval cross section typically has naturally tight curls of about ¼ inch in diameter or less. Such tightly curled hair has proven difficult to safely and consistently relax and re-style into waves or looser curls typically having a diameter of 1 inch or more.

In order to change the configuration of hair from tightly curled or kinked to loosely curled or waved, it is necessary to strip the hair of its tightly curled structure and rebuild the structure of the hair into the new desired configuration. Previous methods of removing the tightly curled structure from hair often left the hair in a severly damaged condition. Often after the hair is restructured into its newly waved or loosely curled construction, the individual is reluctant to wash his or her hair for fear of removing any protective oils from the hair and cause further damage or loss of the desired loose curl or wave.

A typical process employed to re-style tightly curled hair into a new configuration involves first treating the hair with a caustic agent which is absorbed into the hair to break the internal sulfide bonds. It is the sulfide bonds which hold the hair in its tightly curled configuration. Next a test curl is made to determine whether sufficient sulfide bonds have been broken to allow the hair to be re-styled. If the results of the test curl are favorable the hair dresser quickly curls the hair on curling rods. If the test curl fails, the hair dresser conducts a second test curl and continues with a series of curls until the result is favorable. Once curled on the curling rod, a neutralization composition is placed upon the hair to allow the sulfide bonds to reform, thereby retaining the hair in its newly curled configuration.

However, the use of the above method is not precise and often results in under or over processing of the hair. Under processing results in an incomplete recurling of the hair, and over processing results in substantial hair damage and breakage, and generally dull, lifeless and unmanageable hair.

Accordingly, a need exists for a process of re-curling or waving previously tightly curled hair, which significantly reduces the chance of under or over processing of the hair. Further, a need exists for a process of re-curling or waving such hair which results in substantially less damage to the hair.

SUMMARY OF THE INVENTION

The present invention provides a method by which hair which is tightly curled or kinked can be consistently relaxed and reformed into a looser curl or wave configuration, with substantially less damage to the hair. The present invention provides a process for reforming tightly curled hair into a loosely curled or waved configuration comprising the steps of: first, contacting the hair with an aqueous relaxant composition having a pH of between about 8.0 and about 11.0 and comprising at least a major proportion of water and between about 5 to 10 wt-%, based upon the aqueous relaxant composition of a monoethanolamine thioglycolate. Second, rinsing the hair with a neutral aqueous solution so as to remove a substantial portion of the relaxant composition; third, contacting the hair with an aqueous suspending composition having a pH of between about 3.5 and 7.0, the aqueous suspending composition comprising at least a major proportion of water and about 0.0001 to 0.1 wt-% of ammonium chloride and 0.0001 to about 0.1 wt.-% of magnesium chloride, both based on the suspending composition, the suspending composition is preferably rinsed out and reapplied to the hair; fourth, the hair is wrapped onto curling rods; fifth, contacting the hair with a heat generating composition for a period of time and in an amount sufficient to increase the hair temperature to between 100° F. and 130° F. and preferably to between about 110° F. and about 120° F., the heat generating composition comprising a first solution, and a second solution, the first and second solutions are provided in separate containers until application to the hair, when combined the first and second solutions react to produce sufficient heat and provide between about 5 and about 10 wt-% unreacted thioglycolate after reaction between the first and the second solutions is complete; the hair is preferably rinsed with water to rinse most of the heat generation composition from the hair; sixth, contacting the hair with a sufficient amount of an oxidizing composition, such as sodium bromate solution, to oxidize substantially all of the remaining thioglycolate and derivatives; seventh, removing the curling rods; and eighth, contacting the hair with an acidic protein final rinse solution for a period of time and in an amount sufficient to cause the hair to reach substantially a neutral pH.

DETAILED DESCRIPTION OF THE INVENTION

The present invention provides a method by which hair that is tightly curled can be relaxed and reformed into looser curls or waves. Hair which in its natural state has extremely tight curls with diameters of ¼ of an inch and less is typically relatively flat or oval in cross-section.

The process of the present invention comprises contacting the hair with a sufficient amount of an aqueous relaxant composition to relax the tight curl of the hair. The aqueous relaxant composition is believed to relax the tightly curled hair by breaking the disulfide bonds within the hair structure and removing sufficient "memory" of the hair so that the hair can be reformed into a new configuration. The relaxant composition is applied evenly throughout the subject's hair and should preferably be combed until the relaxant composition has been uniformly applied and the hair exhibits a slight residual wave. At this point a cap is preferably placed on the subject's head for roughly 5 minutes. When the subject's hair is particularly coarse or resistant to relaxation, it may be desirable to place the subject's head under a warm air conditioned dryer for the 5 minutes.

After the relaxant composition has been allowed to remain on the subject's head for the necessary duration, as described, the hair should be rinsed thoroughly with warm water to remove most of the relaxant composition from the hair.

The relaxant composition comprises a composition having a pH of between about 8.0 and about 11.0 and preferably between about 9.0 and 10.0, having about 5 to about 10 wt-% of a monoethanolamine thioglycolate. Monoethanolamine thioglycolate is used because it has a gentler action on the hair and provides a substantially odor free product. In a preferred formulation the monoethanolamine thioglycolate is present in the range of between about 7.0% and about 8.0% by weight, and has a free amine concentration of between about 1.0 and 2.0. Such a composition will act to open the cuticle, but will cause a minimum of damage to the hair.

It is also preferred that a suitable amount of a gel forming composition such as CARBOPOL, a polyacrylic acid commercially available from B. F. Goodrich, or its equivalent, be used to provide sufficient viscosity to the relaxant composition. It is advantageous to apply the relaxant composition to the hair temper the action of the monoethanolamine thioglycolate on the hair and to mechanically aid in application of the composition to the subject's hair by increasing lubricity. It is also preferred that the relaxant composition be substantially odor free and less irritating to the subject's scalp.

The relaxant composition of the present invention is applied to the hair of the subject by the operator in an amount which is sufficient to relax the hair to a desired state. The amount of relaxant used will be dependent on the mass of subject's hair, the coarseness of the hair and/or the resistance to relaxation exhibited by the hair. It has been found that a typical application of the relaxant composition is between about 75 and about 125 milliliters and for a duration of about two fifteen minutes.

After the relaxant composition has been rinsed from the subject's hair, the next step in the process of the present invention involves applying a sufficient amount of an aqueous suspending composition to the hair. The suspending composition of the present invention preferably has a pH of between about 3.5 and 7.0 and more preferably between 4.5 and 6.5, most preferably between about 5.0 and 6.0. The suspending composition comprises a major portion of water and between about 0.0001 and 0.1 weight % of ammonium chloride, and between about 0.0001 to 0.1 weight % of magnesium chloride, preferably between about 0.0005 and 0.0015% of both ammonium chloride and magnesium chloride.

In addition, the suspending composition may also contain surfactants and detangling agents which are designed to increase the lubricity of the subject's hair to minimize mechanical damage from manipulation of the hair during processing. Detangling agents suitable for use in the process of the present invention include polyamines, hydrolyzed animal proteins, and fatty acids. The hydrolyzed animal proteins are preferably present between about 2 and about 8 percent by weight, the surfactants are preferably present between about 25 and about 35 percent by weight, the fatty amides are preferably present between about 3 and about 5 percent by weight, and the polyamines are preferably present between about 2 and about 4 percent by weight.

The suspending composition may further include additional proteins or keratins or mixtures thereof which are capable of reacting with the hair during the time when the hair's cuticle is open. The bonding of the proteins and keratins to the hair is very beneficial to the hair at this juncture particularly because they tend to bond to the rough or damaged portions of the hair to strengthen these portions.

Surfactants are preferably included in the suspending composition and act as wetting agents to affect a reduction in the surface tension, thereby causing a deeper penetration of the proteins, keratins, minerals and other additives which are bonded to the hair.

The suspending composition is applied uniformly throughout the hair, and preferably rinsed off and applied a second time. The first application of the suspending composition removes most of the residual relaxant composition from the surface of the hair along with the gel coating which is present if the relaxant composition is in a gel form. The second application is left on the hair to perform its intended function.

After the suspending composition has been applied for the second time, the subject's hair is wrapped about a plurality of permanent wave rods having a desired diameter or diameters. Permanent wave rods are made of various materials, such as plastics, which to not react with the solutions used in the process of the present invention. In addition, permanent wave rods have fastening means that allow the hair to be secured in a desired position about the rod. Permanent wave rods typically vary in diameter from a ¼ of an inch to ¾ of an inch in diameter. The diameter of rod is selected to give the desired curl diameter to the subject's hair.

After the subject's hair has been wrapped about the curling rods a two-part heat generating composition is applied to the hair. This heat source is intended to aid in the opening of the cuticle of the hair within the hair structure and to thereby aid in penetration. This composition is provided as two separate solutions which when combined react exothermically to provide a heated solution which raises the temperature of the hair to a desired temperature. It is desired that the temperature of the hair be raised to a temperature in the range of about 100° F. to about 130° F. and preferably in the range of between about 110° F. and about 120° F.

A suitable first solution of the heat generating composition is a solution of ammonium thioglycolate, free ammonia, and water. A second solution is preferably a hydrogen peroxide solution. The ratio of the equivalents of the reactive component in the first solution, namely the ammonium thioglycolate, and the equivalents of the of the hydrogen peroxide in the second solution, should be such that the heat generating composition will provide between 5 and 10 wt-% of unreacted thioglycolate after the reaction between the first and second solutions is complete with ammonium present at between about 1 and 2 percent. The first solution of the heat generating composition preferably contains between about 10 wt-% and about 20 wt-% ammonium thioglycolate. The second solution preferably contains between about 3 wt-% and about 7 wt-% hydrogen peroxide.

The heat generating composition reaction produces a bi-product, namely, diammonium dithioglycolate which acts to block excessive hair structure damage due to too much free thioglycolate or thioglycolic acid. It is believed that an equilibrium is reached between the thioglycolate and thioglycolic acid and dithioglycolate which prevents further decomposition of the sulfide bonds past a desired end point. Thus, the heat generating composition eliminates overprocessing of the hair's sulfide bonds and eliminates the probability of structural hair damage and depilitation.

The self-timing attribute of this composition is very important because hair has a wide range of porosity and physical geometries, and therefore, processing time for hair, even on different areas of a single hair or areas on a subject's head, may be vastly different. This self-limiting step eliminates the operator's judgment as to the proper processing time and allows for consistent curl restructuring with minimal hair damage. The heat generating composition is typically applied for about two to fifteen minutes before the next step is effected. It is desirable to rinse the heat generating composition thoroughly from the hair.

The next step in the process involves contacting the hair of the subject with an aqueous oxidizing composition, such as a hydrogen peroxide or bromate solution in a sufficient amount to oxidize substantially all of the remaining thioglycolate and thioglycolate derivatives. This step allows for the reforming of the disulfide bonds of the hair into the new configuration as determined by the configuration of the hair about the permanent wave rod. It is believed that the oxidizing composition solution allows the sulfide chain-linkages to be reassembled allowing the hair to have a new memory of its configuration about the rod.

Sodium bromate is a preferred active ingredient in the oxidizing composition because it produces a more springy and tighter curl reformation. In addition, sodium bromate is a stable oxidizing agent which will not decompose as rapidly as other oxidizing agents in storage. The aqueous oxidizing composition preferably contains about 5 wt-% to about 15 wt-% sodium bromate.

After the oxidizing composition has been allowed to soak on the subject's hair for roughly 5 to 20 minutes preferably two to fifteen minutes, the hair is typically rinsed with warm water before the curling rods are removed from the subject's hair.

A final step consists of contacting the subject's hair with an acidic aqueous solution for a period of time and in a sufficient amount to cause the hair to reach a substantially neutral pH. The acidic solution preferably has a pH in the range of between about 4.5 and about 6.5. This mild acidic solution eliminates all of the residual alkali material which may be left in the hair from the previous steps. This final acid rinse also preferably contains hair restructuring components such as proteins, vitamins, cell regenerative agents, and natural protein reconstructors. These additional hair restructuring components are physically entrapped by the hair when added in this acidic aqueous solution and the cuticle of the hair is sealed. A shiny resistant armor to the cortex of the hair fiber is produced.

The acid solution is applied to the subject's head usually after blotting excess moisture from the hair with a towel. The solution is preferably combed gently through the hair and allowed to remain for about 2 to 5 minutes before the excess is blotted from the hair and the hair is styled.

After the hair has been styled and/or cut as desired, it is preferred that a humectant spray be added to the hair to further protect the hair. A humectant spray having a high content of glycerine, preferably about 2 to 15 wt-%, or like material may be applied to the hair to maintain and draw moisture necessary to keep the hair in a soft and moist condition. The hydrophilic properties of this humectant spray aids in retarding natural moisture evaporation which is especially prominent in flat or oval, tightly-curled hair.

In addition, a UV light absorbing compound may be added to this final humectant spray to minimize or eliminate the oxidizing or fading effect caused by sunlight on darker hair. Dark hair is especially prone to damage by ultraviolet rays because of its high light absorbing tendencies. The final moisture retaining spray can also contain additional amounts of protein, quaternary detanglers, cationic surfactants and vitamins which insure that the hair has a source of vital enriching agents which can be absorbed from the continued exposure to the humectant spray to help maintain flexible and soft hair fibers.

Because the process of the present invention recurls the hair without substantial damage to the hair, the subject is free to shampoo his or her hair as desired. Unlike other such processes, the hair will retain its newly curled configuration even after several washings.

The invention is further described in the following non-limiting example.

EXAMPLE 1

The process of the present invention was practiced on a subject having hair with an average length of 5 inches when extended, and which had a tight curl with an average curl radius of approximately a quarter inch. In its natural curled state, the hair stood approximately one inch from the subject's head.

The solutions of the process of the present invention were prepared as follows: 120 milliliters of an aqueous relaxant composition was prepared by mixing 22.5 grams of 40% monoethanolamine thioglycolate, 2.1 grams CARBOPOL 940 (B. F. Goodrich) and 4.8 grams of monoethanolamine in 90 milliliters of deionized water.

Thirty milliliters of an aqueous suspending composition was prepared by mixing 1.5 g proteins, 1.2 g fatty amides, 0.75 g polyamine, 9 g a surfactant, 0.0003 g ammonium chloride, and 0.0003 g magnesium chloride in 17.4 milliliters of deionized water.

The first heat-generating solution was prepared by mixing 26.4 grams of 60.0% ammonium thioglycolate, 3.3 grams of aqueous ammonia 28% in 66.5 milliliters of water.

The second heat-generating solution was prepared by mixing 2.65 g stabilized hydrogen peroxide 35% solution into 18.3 milliliters of deionized water.

The oxidizing solution of the present invention was prepared by mixing 13.57 grams of sodium bromate in 111.86 grams of deionized water.

The final acid rinse solution of the present invention was prepared by mixing 0.53 milliliters of an acid hydrolized protein and diluting it with 20.25 milliliters of deionized water, 42 milligrams of pro-vitamin B5, the final ph was 5.5.

The humectant spray was prepared by mixing 29.5 grams of glycerine, 0.29 milligrams of octadimethyl PABA which is a UV light absorber, 14.9 milligrams of acidic hydrolyzed animal protein, 0.6 milligrams of provitamin B5, 35.5 mg quaternary detanglers and 30.1 milliliters of deionized water.

One hundred twenty milliliters of the relaxant composition at a temperature of 75° F. was combed evenly throughout the subject's hair. The solution was left on the subject's hair for 12 minutes, and then the bulk of the relaxant composition was rinsed from the hair with warm water.

At this time 15 milliliters of the aqueous suspending solution at 75° F. was worked evenly throughout the subject's hair, and rinsed out. An additional 15 milliliters was evenly applied and the subject's hair was rolled about 50 curling rods of 0.45 inch diameter. The first and second heat producing solutions were mixed together and after 2 minutes were applied evenly to the rods throughout the subject's hair. The temperature of the subject's hair was measured at 118° F. after 5 minutes and the temperature stayed at this temperature for 12 minutes.

Fifteen minutes after the heat generating composition was applied, it was rinsed with warm water and blotted dry with a towel. One hundred eighteen milliliters of the oxidizing solution was applied evenly to the rods throughout the subject's hair and left for 15 minutes The temperature of the subject's hair returned to approximately 80° F., was rinsed, the curling rods were removed, and the hair gently rinsed again.

At this time 21 milliliters of the acidic final rinse is added and left on the hair.

The subject's hair was then styled and the humectant spray was sprayed lightly onto the hair. The subject's hair appeared shiny, bouncy, vibrant, and soft and had an average curl diameter of 1¼ inches. When strands of the subject's hair were examined under a microscope at 600 power, the hair had minimal damage and appeared generally healthy and shiny.

What is claimed is:

1. A process for recurling tightly curled hair, comprising the steps of:
   (a) contacting the hair with an effective amount of an aqueous relaxant composition, said aqueous relaxant composition having a pH of between about 8.0 and about 11.0 and comprising between about 5 to about 10 percent by weight of a monoethanolamine thioglycolate based upon the aqueous relaxant composition;
   (b) rinsing the hair with a neutral aqueous composition to remove a substantial portion of said relaxant composition;
   (c) contacting the hair with an aqueous suspending composition having a pH of between about 3.5 and about 7.0, said aqueous suspending composition comprising between about 0.0001 to about 0.1 percent ammonium chloride and about 0.0001 to 0.1 percent magnesium chloride by weight based upon said aqueous suspending composition;
   (d) rolling the hair onto a plurality of curling rods;
   (e) contacting the hair with a heat generating composition for a period of time and in an amount sufficient to increase the temperature of the hair to a temperature in the range of between about 100° F. and about 130° F.; the heat generating composition comprising a first solution and a second solution said first and second solutions provided in separate containers until prior to application to the hair, said heat generating composition containing between about 5 and about 10 percent by weight of unreacted thioglycolate after the reaction of said first and second solutions is complete;
   (f) contacting the hair with a sufficient amount of an aqueous oxidizing composition to oxidize substantially all of the remaining thioglycolate and thioglycolate derivatives;
   (g) removing the curling rods; and
   (h) contacting the hair with an acidic final rinse solution for a period of time and in an amount sufficient to cause the hair to reach substantially a neutral pH.

2. The process of claim 1 further comprising the step of rinsing out said oxidizing composition with water prior to contacting the hair with said final acid rinse.

3. The process of claim 1 further comprising the step of rinsing out said heat generating composition with water after the maximum temperature has been attained but before contacting the hair with said oxidizing composition.

4. The process of claim 1 wherein said aqueous oxidizing composition comprises a 5 to 15 wt-% sodium bromate solution.

5. The process of claim 1 further comprising the step of contacting the hair with a humectant composition after the application of said acid final rinse, said humectant composition comprising about 2 to 15 wt-% glycerin.

6. The process of claim 1 wherein the tightly curled hair subjected to the recurling process has a generally flat or oval cross-section.

7. The process of claim 1 wherein the hair is contacted with
   (i) said relaxant composition for about 2 to 15 minutes before the next step is effected,
   (ii) said heat generating composition for about 2 to 15 minutes before the next step if effected, and
   (iii) said oxidizing composition for about 2 to 15 minutes before the next step is effected.

8. The process of claim 1 wherein said relaxant composition has a pH of between about 9.0 and about 10.0.

9. The process of claim 8 wherein said relaxant composition comprises between about 7.0 and about 8.0 percent by weight of said monoethanolamine thioglycolate.

10. The process of claim 9 wherein said aqueous suspending composition further includes between about 2 and about 8 percent hydrolyzed animal proteins and between about 25 and about 35 percent surfactants by weight.

11. The process of claim 10 wherein said aqueous suspending composition further includes between about 3 and about 5 percent fatty amides and between about 2 and about 4 percent polyamines by weight.

12. The process of claim 1 wherein said relaxant composition further includes a gel forming composition in an amount sufficient to form a gel.

13. The process of claim 1 wherein said suspending composition comprises between about 0.0005 and about 0.0015 percent ammonium chloride by weight.

14. The process of claim 13 wherein said suspending composition comprises between about 0.0005 and about 0.0015 percent magnesium chloride by weight.

15. The process of claim 1 wherein said first solution of said heat generating composition comprises between about 10 and about 20 percent by weight ammonium thioglycolate and said second solution of said heat generating composition comprises between about 3 and about 7 percent by weight hydrogen peroxide.

16. The process of claim 1 wherein said acidic final rinse solution further includes one or more additives selected from the group consisting of proteins, vitamins, cell regenerative agents.

17. The process of claim 5 wherein said humectant composition further includes one or more additives selected from the group consisting of UV light absorbers, proteins, cationic surfactants, and vitamins.

18. A process for recurling tightly curled hair, comprising the steps of:
   (a) contacting the hair with an effective amount of an aqueous relaxant composition, said aqueous relaxant composition having a pH of between about 9.0 and about 10.0 and comprising between about 7 to 8 wt-%, based upon the aqueous relaxant composition of a monoethanolamine thioglycolate;

(b) rinsing the hair with a neutral aqueous composition to remove a substantial portion of said relaxant composition;
(c) contacting the hair with an aqueous suspending composition having a pH of between about 4.5 and about 6.5, said aqueous suspending composition comprising between about 0.0001 to 0.1 wt-% ammonium chloride, between about 0.0001 to 0.1 magnesium chloride, between about 25 and 35% surfactants, between about 2 and about 8 percent hydrolyzed animal proteins, between about 3 and about 5 percent fatty amides, and between about 2 and about 4 percent polyamines by weight based upon said aqueous suspending composition;
(d) rolling the hair onto curling rods;
(e) contacting the hair with a heat generating composition for a period of time and in an amount sufficient to increase the temperature of the hair to a temperature in the range of between about 100° F. and about 130° F.; the heat generating composition comprising a first solution and a second solution said first and second solutions provided in separate containers until prior to application to the hair, said heat generating composition containing about 5 to 10 wt-% unreacted thioglycolate after the reaction of said first and second solutions is complete;
(f) contacting the hair with a sufficient amount of an aqueous oxidizing composition to oxidize substantially all of the remaining thioglycolate and thioglycolate derivatives;
(g) removing the curling rods; and
(h) contacting the hair with an acidic final rinse solution for a period of time and in an amount sufficient to cause the hair to reach substantially a neutral pH; the acidic aqueous solution having a pH of between about 4.5 and about 6.5.

* * * * *

UNITED STATES PATENT AND TRADEMARK OFFICE
CERTIFICATE OF CORRECTION

PATENT NO. : 4,982,750

DATED : January 8, 1991

INVENTOR(S) : Richard Kaitz

It is certified that error appears in the above-identified patent and that said Letters Patent is hereby corrected as shown below:

Column 3, line 15, insert -- as a gel to -- after the word hair

Column 4, line 15, delete "to" and insert -- do --

Column 4, line 41, delete "of the" after the word "equivalents"

Column 7, line 8, insert -- . -- after the word "minutes"

Column 7, line 10, "F," should read -- F., --

Signed and Sealed this

Fourth Day of August, 1992

*Attest:*

DOUGLAS B. COMER

*Attesting Officer*    Acting Commissioner of Patents and Trademarks